US011553640B2

(12) United States Patent
Naylor et al.

(10) Patent No.: US 11,553,640 B2
(45) Date of Patent: Jan. 17, 2023

(54) AGRICULTURAL WEAR MONITORING SYSTEM

(71) Applicant: CNH Industrial Canada, Ltd., Saskatoon (CA)

(72) Inventors: Matthew Stuart Naylor, Saskatoon (CA); Graham Douglas Stuart, Warman (CA)

(73) Assignee: CNH INDUSTRIAL CANADA, LTD., Saskatoon (CA)

( * ) Notice: Subject to any disclaimer, the term of this patent is extended or adjusted under 35 U.S.C. 154(b) by 788 days.

(21) Appl. No.: 16/438,232

(22) Filed: Jun. 11, 2019

(65) Prior Publication Data

US 2020/0390024 A1    Dec. 17, 2020

(51) Int. Cl.
| A01C 14/00 | (2006.01) |
| A01C 5/06 | (2006.01) |
| A01C 21/00 | (2006.01) |
| G01S 17/08 | (2006.01) |
| G01S 13/08 | (2006.01) |

(52) U.S. Cl.
CPC .............. *A01C 14/00* (2013.01); *A01C 5/064* (2013.01); *A01C 21/002* (2013.01); *G01S 13/08* (2013.01); *G01S 17/08* (2013.01)

(58) Field of Classification Search
CPC ........ A01C 5/064; A01C 14/00; A01C 21/002
See application file for complete search history.

(56) References Cited

U.S. PATENT DOCUMENTS

| 7,571,081 B2 | 8/2009 | Faulkner et al. |
| 8,868,985 B2 | 10/2014 | Hackstein et al. |
| 9,609,288 B1 | 3/2017 | Richman et al. |
| 9,667,710 B2 | 5/2017 | Wilbur et al. |
| 9,704,292 B2 | 7/2017 | Priest et al. |
| 10,096,004 B2 | 10/2018 | Viswanath et al. |
| 2010/0281986 A1 | 11/2010 | Toal et al. |

(Continued)

FOREIGN PATENT DOCUMENTS

| CN | 101957889 B | 2/2012 |
| CN | 105469150 A | 4/2016 |

(Continued)

OTHER PUBLICATIONS

Commercial Drones Market 2017 Global Trend Segmentation and Opportunities Forecast to 2022, M2 Presswire, Jul. 12, 2017, 10 pgs, Normans Media Ltd.

(Continued)

*Primary Examiner* — Alicia Torres
*Assistant Examiner* — Ian A Normile
(74) *Attorney, Agent, or Firm* — Rebecca Henkel; Rickard DeMille (57) ABSTRACT

An agricultural implement wear monitoring system that monitors a first component of an agricultural implement. A sensor detects and emits a signal indicative of a first geometric dimension of the first component and/or a second geometric dimension of the first component relative to a second component. A controller couples to the sensor. The controller monitors the first geometric dimension and/or the second geometric dimension, and in response to a detected change in the first geometric dimension and/or the second geometric dimension determines a remaining service life of the first component.

20 Claims, 6 Drawing Sheets

(56) References Cited

U.S. PATENT DOCUMENTS

| | | | |
|---|---|---|---|
| 2014/0316614 A1 | 10/2014 | Newman | |
| 2014/0336791 A1 | 11/2014 | Asenjo et al. | |
| 2015/0170090 A1 | 6/2015 | Bose et al. | |
| 2016/0019560 A1 | 1/2016 | Benkert et al. | |
| 2016/0050840 A1 | 2/2016 | Sauder et al. | |
| 2016/0073573 A1 | 3/2016 | Ethington et al. | |
| 2016/0133066 A1 | 5/2016 | Lavie | |
| 2016/0237640 A1 | 8/2016 | Carpenter et al. | |
| 2016/0253595 A1 | 9/2016 | Mathur et al. | |
| 2017/0011298 A1 | 1/2017 | Pal et al. | |
| 2017/0068246 A1 | 3/2017 | Zang | |
| 2017/0208151 A1 | 7/2017 | Gil et al. | |
| 2018/0137431 A1 | 5/2018 | Goldfarb et al. | |
| 2019/0124824 A1* | 5/2019 | Hubner | A01C 5/064 |
| 2019/0139335 A1* | 5/2019 | Morawitz | G07C 5/0825 |
| 2019/0258271 A1 | 8/2019 | Sporrer et al. | |
| 2020/0146199 A1* | 5/2020 | Pasquier | A01B 63/145 |
| 2020/0364995 A1* | 11/2020 | Kuo | H04W 4/90 |

FOREIGN PATENT DOCUMENTS

| | | | | |
|---|---|---|---|---|
| CN | 106717164 | * | 5/2017 | A01B 63/02 |
| EP | 3150037 | | 4/2017 | |
| EP | 3312095 | | 4/2018 | |
| EP | 3469868 A1 | * | 4/2019 | A01B 63/008 |
| GB | 2354606 A | | 3/2001 | |
| IN | 5037CH2014 | | 9/2015 | |
| WO | 2016123201 | | 8/2016 | |
| WO | 2017075700 | | 5/2017 | |
| WO | WO-2018189480 A1 | * | 10/2018 | A01B 63/111 |
| WO | 2019109191 | | 6/2019 | |
| WO | 2020023269 | | 1/2020 | |
| WO | WO-2020193826 A1 | * | 10/2020 | A01B 63/02 |

OTHER PUBLICATIONS

Application No. PCT/US2019/042275 Preliminary Report on Patentability, dated Jan. 26, 2021, 9 pgs.

NAXT; "10 Most Important Trends that Farm and Agricultural Equipment Dealers Must Look For;" https://www.naxtsolution.com/wp-content/uploads/2018/08/10-most-important-trends-20180724.pdf; Aug. 10, 2018; 8 pages.

IBM; "Product Overview;" https://www.ibm.com/support/knowledgecenter/en/SS7TH3_1.0.2/com.ibm.pmo.doc/overview/c_pmo_prod_over.html; Nov. 6, 2018; 4 pages.

Ruiz-Gonzalez et al; "An SVM-Based Classifier for Estimating the State of Various Rotating Components in agro-Industrial Machinery with a Vibration Signal Acquired from a Signal Point on the Machine Chassis;" https://www.mdpi.com/1424-8220/14/11/20713/htm; Nov. 3, 2014.

Roy et al; "Continuous maintenance and the future—Foundations and technological challenges;" https://www.sciencedirect.com/science/article/pii/S0007850616301986; Jun. 30, 2016; 22 pages.

CSS Electronics; "Predictive Maintenance 4.0—Practical IOT Intro for Vehicles & Machinery;" https://www.csselectronics.com/screen/page/predictive-maintenance-can-bus-iot/language/en; Nov. 6, 2018; 10 pages.

Powell, Joy; "As its precision ag business grows, Deere adds predictive maintenance alerts;" Equipment World; https://www.equipmentworld.com/as-its-precision-ag-business-grows-deere-adds-predictive-maintenance-alerts/; Aug. 22, 2018.

Bell, Leah; "Downtime by the Numnbers: the Cost, the Data and the Benefits of Predictive Maintenance;" Syncron; https://www.syncron.com/downtime-by-the-numbers-the-cost-the-data-and-the-benefits-of-predictive-maintenance/; Nov. 16, 2017; 6 pages.

Freitag, M. et al; "A Concept for the Dynamic Adjustment of Maintenance Intervals by Analysing Heterogeneous Data;" Applied Mechanics and Materials; vol. 794; Sep. 2015; 10 pages.

PCT/US2019/042275 International Search Report and Written Opinion dated Nov. 6, 2019, 15 pgs.

* cited by examiner

AGRICULTURAL WEAR MONITORING SYSTEM

BACKGROUND

The present disclosure relates generally to agricultural implements.

Certain agricultural implements, such as disc drills, may be used to open trenches in a soil surface and to place agricultural product, such as seed or fertilizer, in the trenches. A disc drill may have several row units attached to a frame and arranged in a row. This arrangement may form several parallel rows of deposited agricultural product as the disc drill is pulled through a field by a tractor. Each row unit may include an opener disc that excavates a trench into the soil surface, a product chute configured to deposit the agricultural product into the trench, and a packing wheel configured to pack the displaced soil on top of the agricultural product. Unfortunately, components on the disc drill may wear out and reduce the effectiveness of the disc drill.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the disclosure. Indeed, the disclosure may encompass a variety of forms that may be similar to or different from the embodiments set forth below.

In one embodiment, an agricultural implement wear monitoring system that monitors a first component of an agricultural implement. A sensor detects and emits a signal indicative of a first geometric dimension of the first component and/or a second geometric dimension of the first component relative to a second component. A controller couples to the sensor. The controller monitors the first geometric dimension and/or the second geometric dimension, and in response to a detected change in the first geometric dimension and/or the second geometric dimension determines a remaining service life of the first component.

In another embodiment, an agricultural implement wear monitoring system that includes a sensor that detects and emits a signal indicative of a first geometric dimension of a first component and/or a second geometric dimension of the first component relative to a second component. A controller couples to the sensor. The controller monitors the first geometric dimension and/or the second geometric dimension, and in response to a detected change in the first geometric dimension and/or the second geometric dimension determines a remaining service life of the first component.

In another embodiment, a method of monitoring wear of an agricultural component. The method includes a first geometric dimension of a first agricultural component and/or a second geometric dimension. The second geometric dimension is a position of the first agricultural component relative to a second agricultural component. The method determines an agricultural field to be worked. The method determines the remaining wear of the first agricultural component and/or the second agricultural component in response to a detected first geometric dimension and/or the second geometric dimension and the agricultural field to be worked.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Any examples of operating parameters and/or environmental conditions are not exclusive of other parameters/conditions of the disclosed embodiments.

The present disclosure is generally directed to agricultural implements, such as disc drills, capable of deposited agricultural product into a field. Disc drills may form several parallel trenches in the surface of a field as the disc drill is towed in a direction of travel, deposits agricultural product(s) within each trench, and packs displaced soil over the deposited agricultural product. The disc drill may include several row units, and each may form a respective trench as a disc of the respective row unit displaces soil. Each row unit may also include components (e.g. a product chute) that enable placement of an agricultural product, such as seed or fertilizer, in the respective trench. Each row unit may also include an independent packer wheel that packs the displaced soil onto the deposited agricultural product to cover the respective trench formed by the disc.

During operation of the disc drill, various components may wear due to contact with the soil. For example, the coulter disc (e.g., cutting disc) may erode from contact with the soil as it cuts the trench. As the coulter disc erodes its diameter changes (e.g., decreases), which may reduce the ability of the coulter disc to cut a trench in the soil. Scrapers and knives on the disc drill may similarly erode from contact with the soil. In order to maintain the effectiveness of the disc drill, an operator may perform various maintenance tasks on the disc drill. For example, the operator may replace the coulter discs, sharpen the coulter discs, adjust the position of the scrapers relative to the coulter discs, replace knives, among others.

As will be explained below, the embodiments below describe an agricultural wear monitoring system that detects wear of one or more components on the disc drill and alerts the operator of the wear. In some embodiments, the agricultural wear monitoring system may also predict or determine the remaining life of the agricultural components in response to soil conditions, weather, current wear of the agricultural components, among others. An owner and/or operator may therefore determine and/or schedule maintenance tasks (e.g., order parts, replace parts, machine parts) to enable the disc drill to remain operational during desired times (e.g., soil preparation season, planting season).

Figure 1:
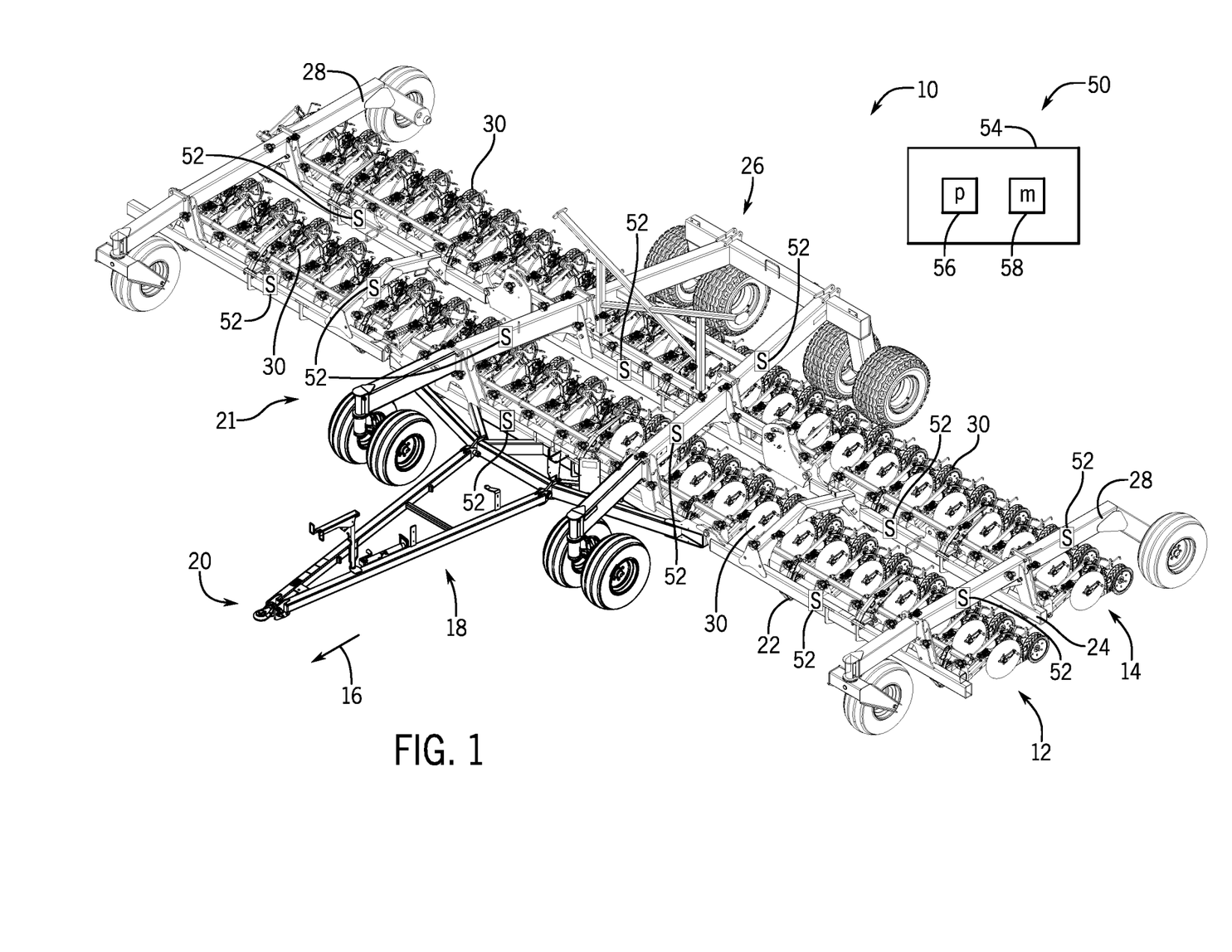
FIG. 1 is a perspective view of a disc drill with two rows of staggered row units, in accordance with an embodiment of the present disclosure.

Referring now to the drawings, FIG. 1 is a perspective view of a disc drill 10 with two rows 12, 14 of row units. The disc drill 10 may be towed by a tractor in a direction of travel 16. In the illustrated embodiment, the disc drill 10 includes an A-frame 18 and a hitch assembly 20, which may be coupled to a corresponding hitch assembly of the tractor. The A-frame 18 is coupled to a main frame 21 of the disc drill 10. In addition, the main frame 21 includes a first frame element 22 that supports a first row 12 of row units and a second frame element 24 that supports a second row 14 of row units. The frame elements 22 and 24 are connected to each other and supported by a central frame section 26 and side frame sections 28 of the main frame 21. Wheels are coupled to the central frame section 26 and the side frame sections 28 to facilitate movement of the disc drill 10 through the field. It should be understood that, while the disc drill 10 includes forty-eight row units 30, arrangements with any number of row units 30 may be employed.

As explained above, various components of the disc drill 10 experience wear as they contact soil during agricultural operations. In order to detect the wear on these components, the disc drill 10 may include an agricultural wear monitoring system 50. The agricultural wear monitoring system 50 includes one or more sensors 52 that couple to a computer system 54 (e.g., wired connection, wireless connection). The sensors 52 may couple to the computer system 54 wirelessly and/or with a wired connection. These sensors 52 may include LIDAR, radar, Hall effect sensors, position sensors, among others. In operation, these sensors 52 provide a signal indicative of a condition of one or more components on the disc drill 10. This signal is then transmitted to the computer system 54 for processing. The computer system 54 may be located on the disc drill 10, on a tractor coupled to the disc drill 10, and/or a remote location (e.g., maintenance facility).

The computer system 54 may include a processor 56, such as the illustrated microprocessor, and a memory device 58. The computer system 54 may also include one or more storage devices and/or other suitable components. In operation, the processor 56 may be used to execute software, such as software for determining the condition (e.g., extent of wear) of one or more components on the disc drill 10. In response to the detected condition of the components, the computer system 54 may determine a remaining life for the component. In some embodiments, the computer system 54 may also receive additional data from other sources that enable the computer system 54 to determine a remaining life of the component. For example, the computer system 54 may access soil condition data, weather data, historical wear data of the components, among others. In response to determining a remaining life of the component(s), the computer system 54 may alert the operator, produce a work order, schedule maintenance, order parts, and/or a combination thereof.

The processor 56 may include multiple microprocessors, one or more "general-purpose" microprocessors, one or more special-purpose microprocessors, and/or one or more application specific integrated circuits (ASICS), or some combination thereof. For example, the processor 56 may include one or more reduced instruction set (RISC) processors.

The memory device 58 may include a volatile memory, such as random-access memory (RAM), and/or a nonvolatile memory, such as read-only memory (ROM). The memory device 58 may store a variety of information and may be used for various purposes. For example, the memory device 58 may store processor executable instructions (e.g., firmware or software) for the processor 56 to execute, such as instructions for comparing a current image of an agricultural component to an image of a new agricultural component to detect wear. The storage device(s) (e.g., nonvolatile memory) may include ROM, flash memory, a hard drive, or any other suitable optical, magnetic, or solid-state storage medium, or a combination thereof. The storage device(s) may store data, instructions, and any other suitable data.

Figure 2:
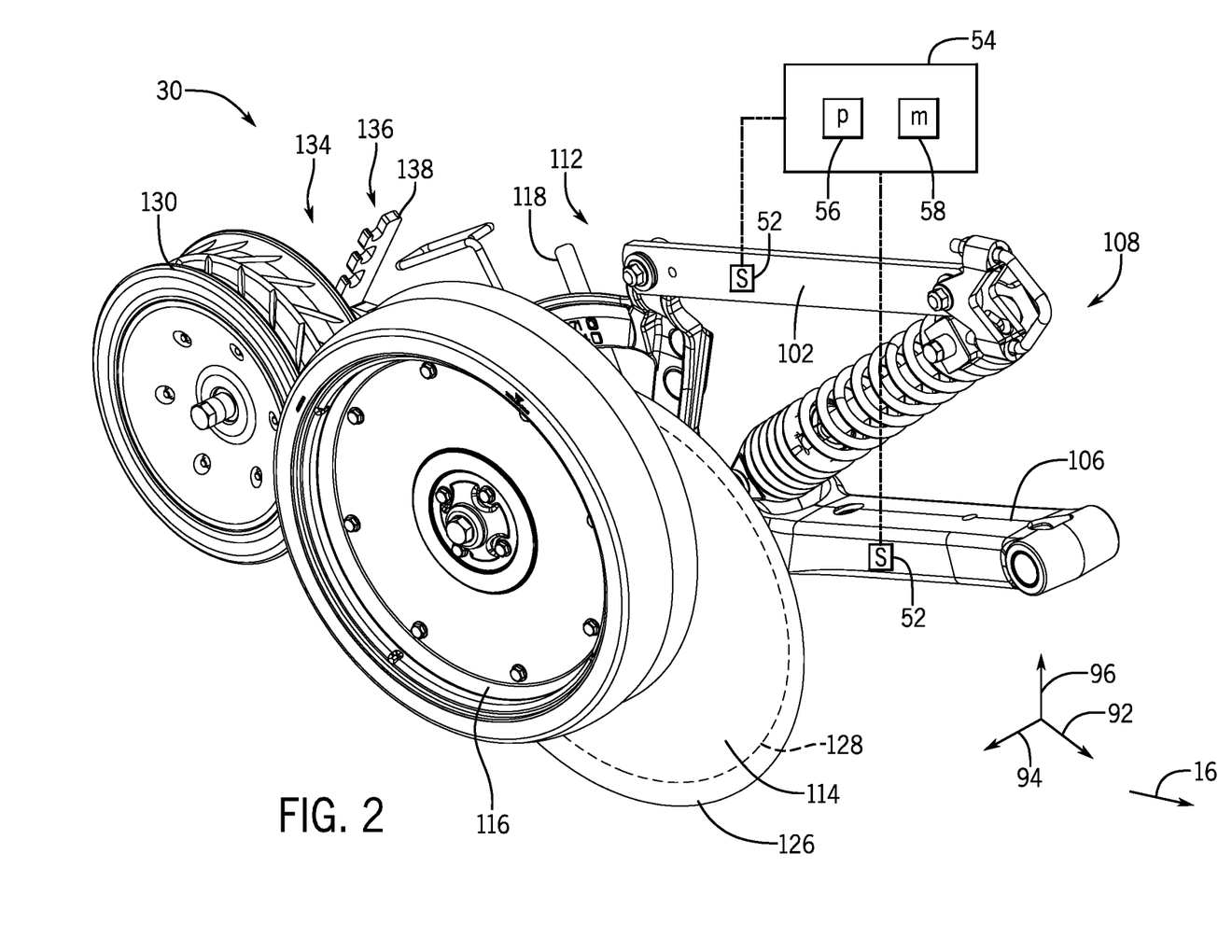
FIG. 2 is a perspective view of a disc drill row unit which may be used in the disc drill of FIG. 1, in accordance with an embodiment of the present disclosure.
Figure 3:
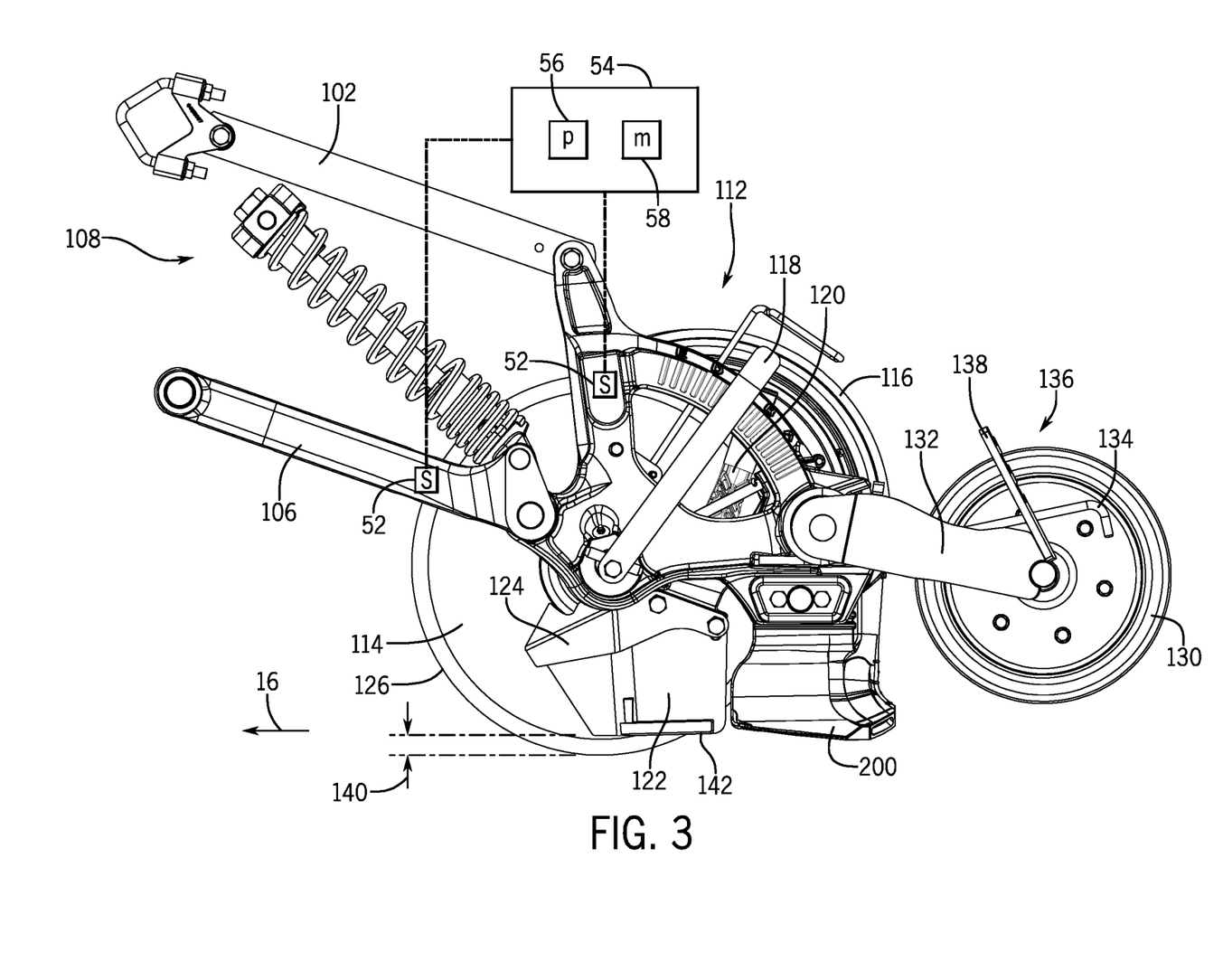
FIG. 3 is a side view of the disc drill row unit of FIG. 2, in accordance with an embodiment of the present disclosure.
Figure 4:
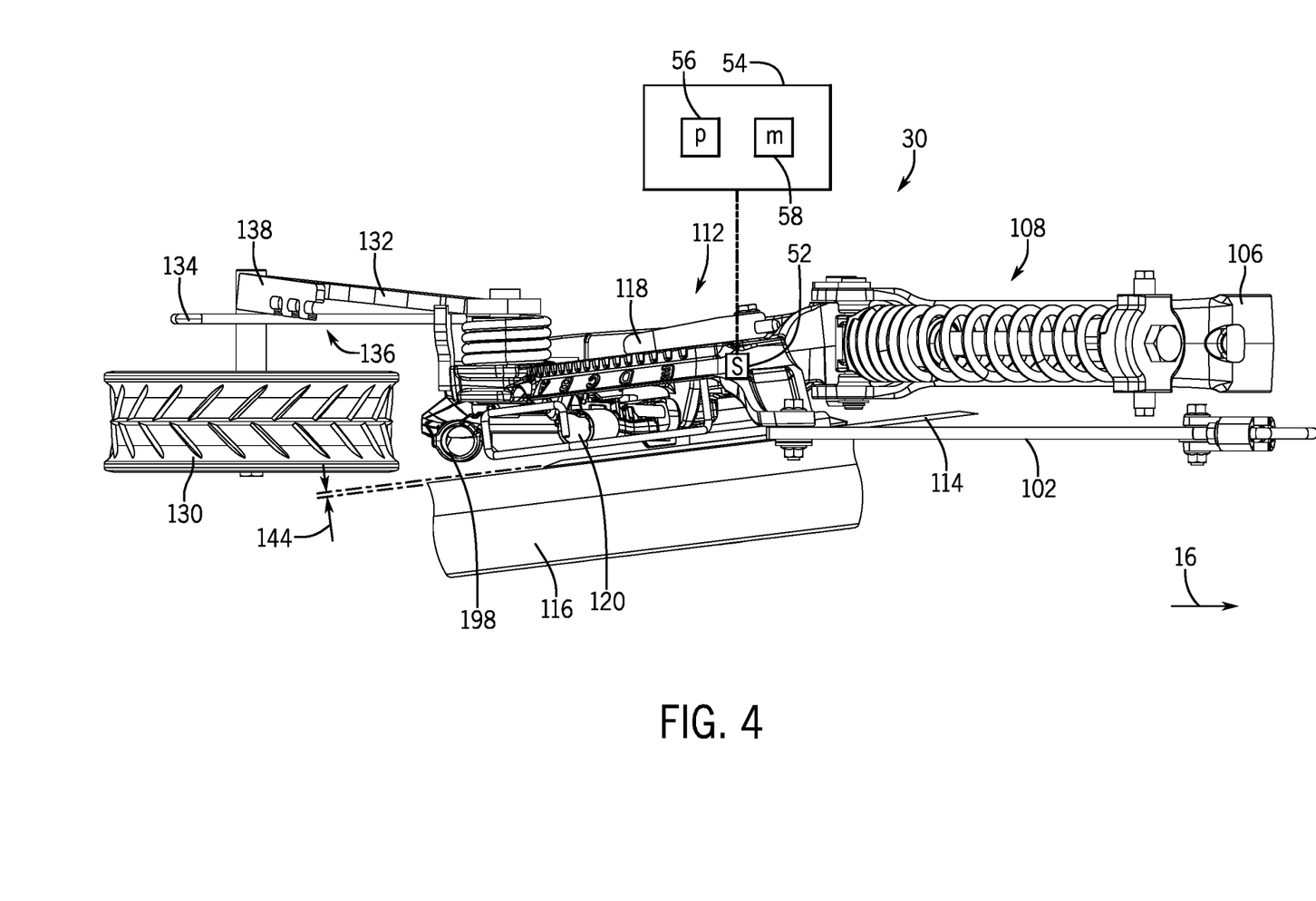
FIG. 4 is a top view of the disc drill row unit of FIG. 2, in accordance with an embodiment of the present disclosure.

FIGS. 2, 3, and 4 are views of a row unit 30 that may be used in the disc drill of FIG. 1. More specifically, FIG. 2 is a perspective view of the row unit 30, FIG. 3 is a side view of the row unit 30, and FIG. 4 is a top view of the row unit 30. The row unit 30 may be described with reference to a longitudinal axis or direction, 92, a lateral axis or direction 94, and a vertical axis or direction 96.

The row unit 30 includes, links 102 and 106 and a damping assembly 108 (e.g., including a spring and a damper) that are configured to couple a frame 112 of the row unit 30 to the disc drill frame 21. The damping assembly 108 may be configured to force the frame 112 against the soil surface. Damping assembly 108 may also be configured to damp upward movement of the frame 112 as the row unit 30 encounters uneven ground. A disc 114 is rotatably coupled to the frame 112. The disc 114 is configured to form a trench in the soil. The depth of the trench may be controlled by the position of the disc 114 relative to a gauge wheel 116 along the vertical axis 96. The vertical position of the gauge wheel 116 may be controlled by a depth regulator handle 118, which in turn changes the depth that the disc 114 cuts the trench in the soil. An agricultural product (e.g., seed or fertilizer) may be disposed within the trench formed by disc 114 via a product chute or conduit 120 (seen in FIG. 3). As the disc 114 displaces soil, a scraper 122 (seen in FIG. 3), attached to the frame 112 with a trash guard 124 (seen in FIG. 3), may direct the flow of soil away from the formed trench and remove soil from the disc 114 (seen in FIG. 3).

In operation, the disc 114 and scraper 122 may wear due to abrasive contact with the soil (seen in FIG. 3). For example, over time the disc 114 (e.g., coulter disc) may gradually reduce in diameter from a first diameter 126 to a second diameter 128. As the diameter of the disc 114 decreases in size, the disc 114 may become less effective at cutting plant residue as it forms the trench. As a result, the ability of the disc 114 to cut a trench may diminish, and in some situations the disc 114 may instead plow the field. In addition, a decrease in the diameter of the disc 114 may lower the scraper 122 into the soil, which may increase contact between the soil and the scraper 122 and thus wear the scraper 122.

Closing wheel 130 couples to the frame 112 with linkage 132. The closing wheel 130 may be substantially laterally aligned with disc 114 to cover a trench formed by disc 114 as the row unit 30 moves in direction of travel 16. The frame 112 also supports a spring 134 (seen in FIG. 3) that urges the closing wheel 130 toward the soil surface. The torque applied by the spring 134 may be adjusted by placing an end of the spring 134 in one of a set of slots 136 in an adjustment plate or bar 138. The pressure of closing wheel 130 may therefore be adjusted depending on the soil type, the agricultural product dispensed, etc.

In order to detect wear of the disc 114, scraper 122, and other agricultural components, the agricultural wear monitoring system 50 includes sensors 52. These sensors 52 may couple to the row unit 30 at various locations that enable wear measurement and/or detection of agricultural components on the row unit 30. For example, the sensors 52 may couple to various arms, bars, shafts of the row unit 30 as well as the frames and/or bars of the implement 10. As explained above, these sensors 52 may include LIDAR sensors, radar sensors, visual sensor (e.g., camera), Hall effect sensors, or a combination thereof. For example, a LIDAR sensor may emit laser light that measures a distance between the agricultural component (e.g., disc 114, scraper 122) and the sensor. By detecting this distance, the computer system 54 may detect changes in one or more dimensions of the agricultural component and/or a distance between one or more components (e.g., width, length, diameter). A radar sensor may similarly be used to detect changes in the dimensions of agricultural components or distances between components by emitting and detecting radio waves.

A visual sensor may also be used to detect the wear of components. For example, the visual sensor may capture images of the components. These images may then be compared to images without wear with the computer system 54. The computer system 54 may then determine the wear by detecting the differences in these images. For example, artificial intelligence may analyze these images and determine changes in wear, the extent of wear, etc. Visual sensors may also detect the presence and/or absence of wear markings that enable wear detection. For example, the visual sensor may detect markings such as symbols, letters, numbers, etc. on the disc 114. In one example, the disc 114 may include these markings, and as the disc 114 erodes away (e.g., reduces in diameter) the markings may likewise wear away. As the visual sensor captures these images, the computer system 54 detects the absence of the markings, enabling the computer system 54 to recognize wear. For example, the disc 114 may have multiple markings at different diameters (e.g., 18 inches, 17.5 inches, 17 inches, 16.5 inches, 16 inches) as progressively more and more markings are eroded away the computer system 54 is able to track and determine the extent of the wear.

In some embodiments, a Hall effect sensor may be used to detect wear of components. For example, a Hall effect sensor may detect the presence of an outer diameter of the disc 114 (e.g., metal disc 114). As the disc 114 wears away during use, the Hall effect sensor may no longer detect the presence of disc 114. By detecting the absence of the outer diameter of the disc 114 or even a weak metal signature, the computer system 54 may determine the extent of wear on the disc 114.

As explained above, the agricultural wear monitoring system 50 may also detect wear by monitoring the distances between components. For example, the agricultural wear monitoring system 50 may use one or more sensors 52 to detect distance 140 between an end 142 of the scraper 122 and the outermost diameter of the disc 114. By detecting this distance 140, the agricultural wear monitoring system 50 is able to detect wear of the disc 114 and/or the scraper 122. For example, if the distance 140 increases or decreases outside of a threshold distance, the agricultural wear monitoring system 50 may determine that excess wear has occurred with either the disc 114 and/or the scraper 122. The disc drill 10 and/or the row unit 30 may therefore undergo maintenance. For example, the disc 114 and/or the scraper 122 may be replaced and/or the position of the scraper 122 may be adjusted relative to the outermost diameter (e.g., changed diameter) of the disc 114.

In some embodiments, a distance 144 between the disc 114 and the gauge wheel 116 may be monitored to detect wear. For example, an increase in the distance 144 outside of a threshold distance may indicate wear of the gauge wheel 116 and/or the discs 114. As this distance 144 increases, mud and dirt may enter the gap, which may hinder rotation of the gauge wheel 116 and/or the disc 114 and thus the ability to cut a trench (e.g., the gauge wheel 116 and/or disc 114 may then plow the field).

The use of mirror image parts may also facilitate monitoring and wear detection of one or more components of the row unit 30. For example, only one of the discs 114 may be monitored on each row 12, 14 to determine the wear of all the discs 114 on that row, or in a particular section of the row 12, 14. Likewise, only one of the scrapers 122 may be monitored for wear. In some embodiments, a subset of all of the scrapers, discs, knives, etc. of the disc drill 10 may be monitored to determine maintenance issues for the entire disc drill 10. For example, only the components of every second row unit, third row unit, fourth row unit, fifth row unit, etc. may monitored to determine overall wear of the components on the disc drill 10.

Figure 5:
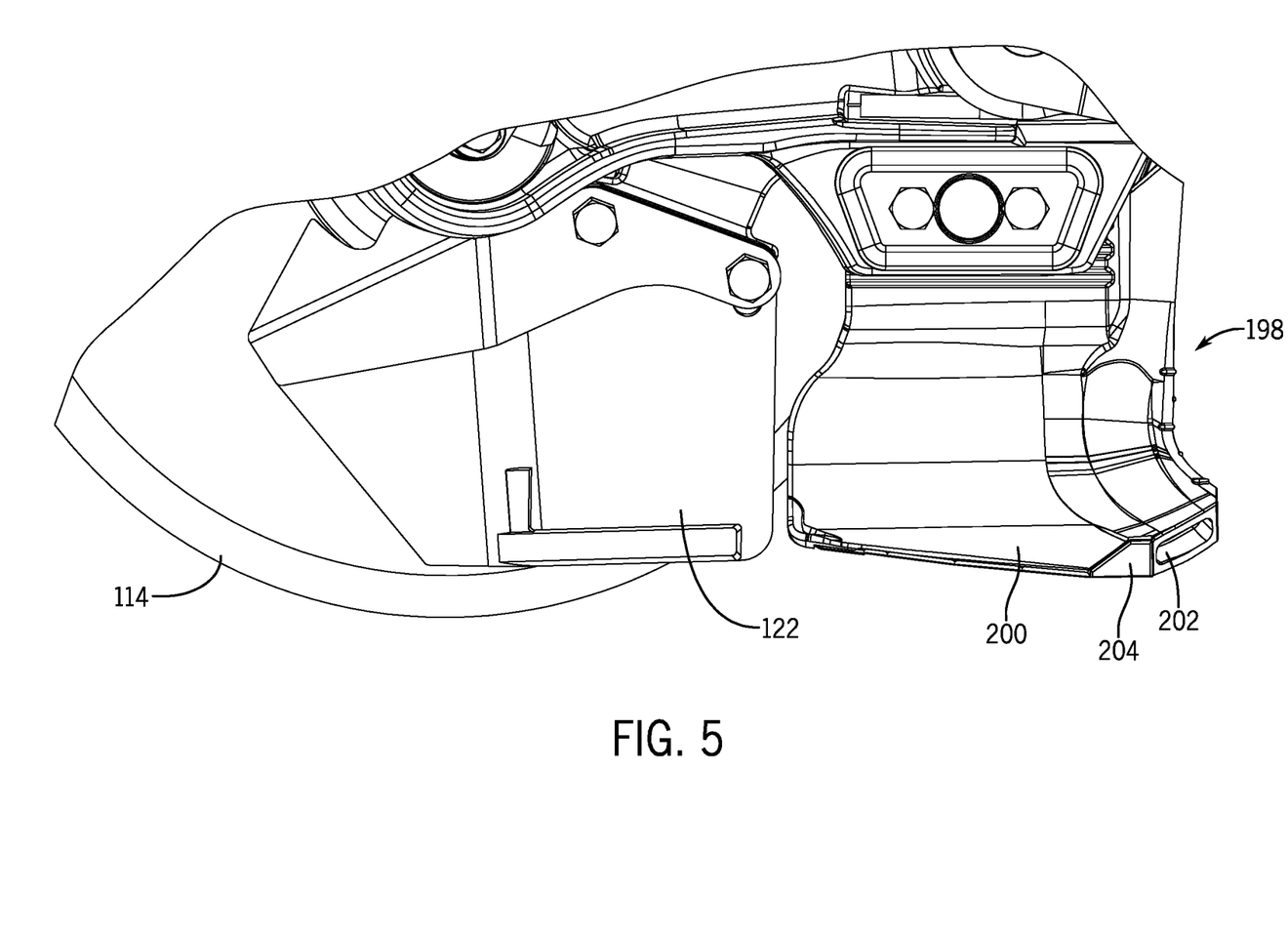
FIG. 5 is a partial side view of a disc drill row unit, in accordance with an embodiment of the present disclosure.

FIG. 5 is a partial side view of the disc drill row unit 30. In some embodiments, a conduit 198 may couple to a knife 200. In operation, the knife 200 may widen the trench formed by the disc 114 to facilitate deposition of particulate in the trench. That is, particulate may flow through the conduit 198 to the knife 200, which then directs the particulate to the outlet 202. Over time, contact between the soil and the knife 200 may erode a side surface 204 of the knife 200. This erosion may increase the size of the aperture or outlet 202, which may enable mud, dirt to enter the outlet 202 blocking the flow of particulate through the knife 200. Accordingly, the agricultural wear monitoring system 50 may use one or more sensors 52 described above to monitor the wear of the knife 200.

Figure 6:
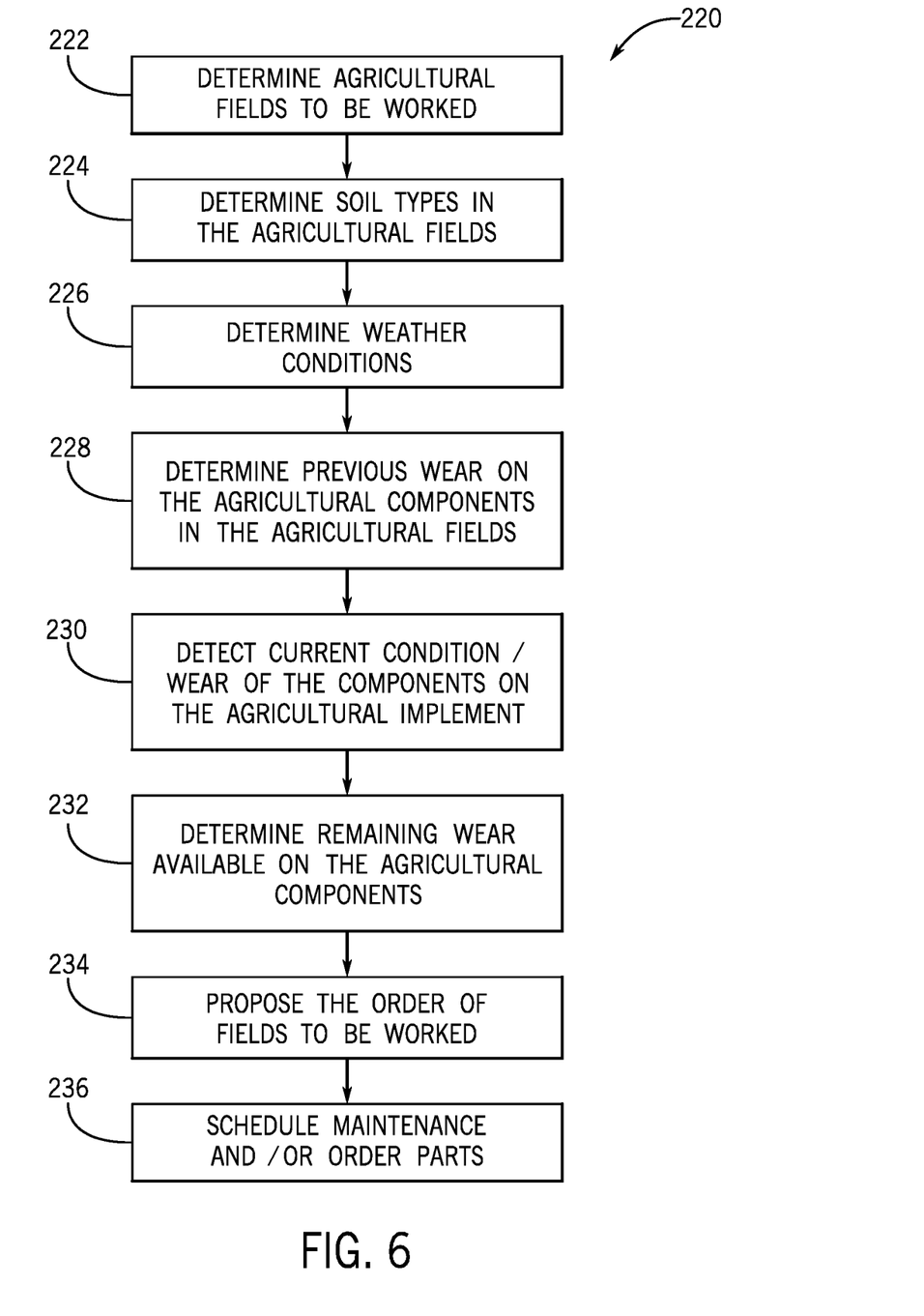
FIG. 6 is a flow chart of a method for determining the life of a component(s) on a disc drill, in accordance with an embodiment of the present disclosure.

FIG. 6 is a flowchart of a method 220 for determining and/or predicting wear on agricultural components of a disc drill 10. It should be understood that the method 220 may be used to determine and/or predict wear for other agricultural components (e.g., planters, combines). While seven steps are discussed and illustrated in FIG. 6, it should be understood that some or all of these steps may be used to determine and/or predict wear of agricultural components.

The method 220 may begin by determining which agricultural fields will be worked, step 222. For example, an operator may have a designated number of fields that need to be worked. The acreage and locations of these fields may be stored in the agricultural wear monitoring system 50. For example, they may be programmed into the agricultural wear monitoring system 50 or uploaded to the agricultural wear monitoring system 50 by an operator. As these fields are worked (e.g., planted, fertilized) the agricultural wear monitoring system 50 determines which fields have been worked and which ones have not. The agricultural wear monitoring system 50 may determine this via GPS and/or operator input. The method 220 may then determine the soil types in the remaining fields (e.g., sandy soil, clay soil, silt soil, loamy soil), step 224. This information may be similarly programmed into and/or uploaded to the agricultural wear monitoring system 50. The types of soil in these fields may influence the level of wear on the agricultural components. For example, a sandy soil may more rapidly wear the agricultural components as the agricultural components contact the hard sand in the soil.

The method may then determine the weather conditions for the agricultural fields, step 226. By determining the actual or predicted weather, the method 220 may take into account the effect of soil moisture on the wear of the agricultural components. For example, dry soil may increase the hardness of the soil and the resistance of the soil to agricultural components in contact with the soil, thus accelerating wear of the agricultural components. However, if the predicted or actual weather is wet, the soil will be expected to be moist. Moist or wet soil may reduce the hardness and the corresponding resistance of the soil to agricultural components in contact with the soil. Wet weather may therefore decrease wear on the disc drill 10 and its associated agricultural components that contact the soil. The predicted weather may be determined for any time period before working the fields (e.g., year, month, week, day). In some embodiments, the predicted weather may be based on an average rainfall over several years for the area containing the agricultural fields.

After determining the weather, the method 220 may determine the previous or historical wear of the agricultural components. In some embodiments, the previous wear of the agricultural components may be the historical wear of the agricultural components in the actual agricultural fields that will be worked, step 228. For example, as the disc drill 10 is used to repeatedly work the same fields, agricultural component wear data may be collected to determine wear rates (e.g., average wear rates) in different conditions in those specific fields. The historical wear may also include wear rates of agricultural components collected while testing the agricultural components in different soil types (e.g., sandy soil, clay soil, silt soil, loamy soil). Wear rates in these different soil types may then be used to determine an expected wear rate in the agricultural fields to be worked depending on their soil type.

The method 220 may also use feedback from the sensors 52 to determine the current wear or wear condition of the agricultural components, step 230. For example, the method 220 may determine the wear condition of the discs, scrapers, knives, or a combination thereof. The wear condition may be determined by looking at some or all of the agricultural components on the disc drill or another piece of agricultural equipment. As explained above, all or a subset of the agricultural components may be monitored to determine the wear condition of the agricultural components. In other words, some of the agricultural components may be monitored and the detected wear of the monitored agricultural components may be then attributed to the unmonitored agricultural components. In some embodiments, an operator may determine the wear of the agricultural components and then inputs and/or uploads this information to the agricultural wear monitoring system 50. For example, an operator may measure the diameter of the discs, the length of the scrapers, the size of the knife openings and then input this information into the agricultural wear monitoring system 50.

After receiving all or some of the information in steps 222, 224, 226, 228, and 230, the method 220 determines or predicts the remaining life of the agricultural components, step 232. The remaining life of the agricultural components may be provided to an operator in terms of acres that can be worked with different soil types, hours of usage, and/or how many acres of specifically designated field(s) can be worked before maintenance operations. The ability to determine how much life remains before maintenance operations, enables an operator or owner to schedule maintenance at desired times. For example, if the agricultural wear monitoring system 50 determines that all or a desired number of fields cannot be worked before maintenance is needed, the operator or owner may perform maintenance before starting agricultural operations (e.g., planting, fertilizing). In this way, the method 220 may enable continuous agricultural operations during desired times (e.g., planting season) were interruptions may negatively influence agricultural production. In other words, the operator and/or owner may schedule maintenance of the agricultural implement (e.g., disc drill 10) during times when the agricultural implement is not needed for agricultural tasks.

After determining the remaining wear available on the agricultural components, the method 220 may determine the order of the fields and/or portions of the fields to be worked, step 234. For example, the method 220 may prioritize the fields and/or portions of fields to be worked based on the predicted wear that will occur to the agricultural components. For example, if the conditions of some fields or portions of fields are known to increase the wear on the agricultural components, those fields and/or portions may be worked after working fields that create less wear on the agricultural components. In this way, the method 220 may increase usage and/or delay maintenance.

In some embodiments, the method 220 may automatically schedule maintenance and/or order parts for the agricultural implement (e.g., disc drill 10), step 236. For example, after detecting a threshold level of wear, the agricultural wear monitoring system 50 may automatically order one or more agricultural components for replacement. By detecting and ordering in advance, the method 220 may reduce the downtime of the agricultural implement as maintenance may be rapidly completed without waiting for parts to arrive. In some situations, a drone may control operation and movement of the agricultural implement. The agricultural wear monitoring system 50 may communicate directly with the drone. In response to feedback from the agricultural wear monitoring system 50, the drone may then take the agricultural implement to a maintenance shop at the appropriate time.

While only certain features of the disclosure have been illustrated and described herein, many modifications and changes will occur to those skilled in the art. It is, therefore, to be understood that the appended claims are intended to cover all such modifications and changes as fall within the true spirit of the disclosure.

The invention claimed is:
1. An agricultural implement wear monitoring system, comprising:
 a first component configured to couple to an agricultural implement;
 a sensor configured to detect and emit a signal indicative of a first geometric dimension of the first component and/or a second geometric dimension of the first component relative to a second component; and a controller coupled to the sensor, wherein the controller is configured to monitor the first geometric dimension and/or the second geometric dimension and, in response to a detected change in the first geometric dimension and/or the second geometric dimension, determine a remaining service life of the first component;

wherein the controller is configured to determine an order of fields and/or portions of the fields to be worked in response to determining the remaining service life of the first component.

2. The agricultural implement wear monitoring system of claim 1, wherein the first component comprises a disc configured to form a trench in a soil surface.

3. The agricultural implement wear monitoring system of claim 2, wherein the first geometric dimension comprises a diameter of the disc.

4. The agricultural implement wear monitoring system of claim 2, wherein the second component comprises a gauge wheel.

5. The agricultural implement wear monitoring system of claim 4, wherein the second geometric dimension comprises a distance between the disc and the gauge wheel.

6. The agricultural implement wear monitoring system of claim 2, wherein the second component comprises an agricultural scraper.

7. The agricultural implement wear monitoring system of claim 6, wherein the second geometric dimension comprises a distance between an outer diameter of the disc and a tip of the agricultural scraper.

8. The agricultural implement wear monitoring system of claim 1, wherein the first component comprises an agricultural knife with an outlet.

9. The agricultural implement wear monitoring system of claim 8, wherein the first geometric dimension comprises an area of the outlet.

10. The agricultural implement wear monitoring system of claim 1, wherein the sensor comprises a laser, a camera, a hall effect sensor, radar, and/or LIDAR.

11. An agricultural implement wear monitoring system, comprising:

a sensor configured to detect and emit a signal indicative of a first geometric dimension of a first component and/or a second geometric dimension of the first component relative to a second component; and a controller coupled to the sensor, wherein the controller is configured to monitor the first geometric dimension and/or the second geometric dimension and, in response to a detected change in the first geometric dimension and/or the second geometric dimension, determine a remaining service life of the first component;

wherein the controller is configured to determine an order of fields and/or portions of the fields to be worked in response to determining the remaining service life of the first component.

12. The agricultural implement wear monitoring system of claim 11, wherein the controller accesses geographic soil conditions and includes geographic soil conditions in determining the remaining service life of the first component.

13. The agricultural implement wear monitoring system of claim 11, wherein the controller accesses weather data and includes weather data in determining the remaining service life of the first component.

14. The agricultural implement wear monitoring system of claim 11, wherein the remaining service life of the first component is calculated in operation time of the first component.

15. The agricultural implement wear monitoring system of claim 11, wherein the remaining service life of the first component is calculated in acres of use.

16. The agricultural implement wear monitoring system of claim 11, wherein the first component comprises a disc configured to form a trench in a soil surface, and the first geometric dimension comprises a diameter of the disc.

17. The agricultural implement wear monitoring system of claim 11, wherein the first component comprises a disc configured to form a trench in a soil surface, the second component comprises an agricultural scraper, and the second geometric dimension comprises a distance between an outer diameter of the disc and a tip of the agricultural scraper.

18. The agricultural implement wear monitoring system of claim 11, wherein the first component comprises an agricultural knife with an outlet, and the first geometric dimension comprises an area of the outlet.

19. The agricultural implement wear monitoring system of claim 1, wherein the controller accesses geographic soil conditions and includes geographic soil conditions in determining the remaining service life of the first component.

20. The agricultural implement wear monitoring system of claim 1, wherein the controller accesses weather data and includes weather data in determining the remaining service life of the first component.

* * * * *